United States Patent [19]
Smith et al.

[11] Patent Number: 4,735,626
[45] Date of Patent: Apr. 5, 1988

[54] AIR FRESHENER UNIT

[75] Inventors: Brian R. Smith, Bamford; Arthur W. R. Balkham, King'Lynn, both of England

[73] Assignees: Reckitt & Colman Products Limited, London; Porvair Limited, King's Lynn, both of England

[21] Appl. No.: 70,247

[22] Filed: Jul. 6, 1987

Related U.S. Application Data

[63] Continuation of Ser. No. 779,436, Sep. 24, 1985, abandoned.

[30] Foreign Application Priority Data

Sep. 29, 1984 [GB] United Kingdom ................ 8424653

[51] Int. Cl.$^4$ .......................... C11D 1/65; A46B 17/00
[52] U.S. Cl. ...................................... 8/137; 15/257 B; 134/21; 521/55; 521/918; 521/919; 512/4
[58] Field of Search .......................... 15/257 B; 8/137; 134/21; 252/522 A; 521/55, 918, 919

[56] References Cited

U.S. PATENT DOCUMENTS

| Re. 27,917 | 2/1974 | Jefferson et al. | 521/99 |
|---|---|---|---|
| 3,336,244 | 8/1967 | Rockoff | 521/63 |
| 3,450,650 | 6/1969 | Murata | 521/99 |
| 3,491,173 | 1/1970 | Kobsa | 521/55 |
| 3,688,985 | 9/1972 | Engel | 521/55 |
| 3,730,916 | 5/1973 | Etchells, III | 521/55 |
| 3,876,762 | 4/1975 | Rabussier et al. | 424/28 |
| 4,226,944 | 10/1980 | Stowe et al. | 521/76 |
| 4,339,550 | 7/1982 | Palinczar | 521/99 |

Primary Examiner—Morton Foelak
Attorney, Agent, or Firm—Bacon & Thomas

[57] ABSTRACT

New dynamic air freshener unit comprises a porous synthetic polymer support impregnated with a fragrance. The synthetic polymer support is one produced by:
(a) bonding together small particles of solid polymer;
(b) coagulating polymer solutions in a non-solvent for the polymer; or
(c) expanding a thermoplastic or thermosetting plastic by means of a blowing agent; to form a porous body.
The unit is especially useful in vacuum cleaners.

2 Claims, No Drawings

AIR FRESHENER UNIT

This application is a continuation of application Ser. No. 779,436 filed Sept. 24, 1985, now abandoned.

The present invention relates to a novel air freshener unit.

Fragrance-impregnated paper filters and/or sheaves of fibres, in cylindrical form, have been proposed for use as air fresheners in conjunction with vacuum cleaners. However, the level of consistency with which these known filters release fragrance is inadequate from the point of view of the user.

We have now found a novel air freshener unit which overcomes the abovementioned disadvantage of known air freshener units and which will release fragrance at levels more acceptable to users of such units.

Accordingly, the present invention provides a dynamic air freshener unit comprising a porous, synthetic polymeric support impregnated with a fragrance, wherein the synthetic polymeric support is one produced by (a) bonding together small particles of solid polymer; (b) coagulating polymer solutions in a non-solvent for the polymer; or (c) producing a thermoplastic or thermoset porous plastic by means of a blowing agent.

By the term "dynamic air freshener unit" as used in the present specification and claims, we mean an air freshener unit which, in use, will release fragrance by the passage of air over it, said air movement caused by the application of differential air pressure. Instances of applications in which the dynamic air freshener units of the invention find use are in air conditioning systems, e.g. in vehicle or room ventilation systems and, especially, in vacuum cleaners.

In order to retain the optimal amount of fragrance on the support between the point of manufacture of the unit of the invention and its point of use, the unit is preferably packaged over the period between manufacture and use. The form of packaging may be any convenient form comprising an envelope of material impermeable to the fragrance and its components sealed against loss of fragrance. One suitable form is a sealed envelope comprising a film of impermeable polymeric material, especially an envelope comprising a laminate of aluminium foil and a polymeric material.

The porous synthetic polymeric support component of the unit of the invention is characterised by comprising a polymer lattice containing within its structure a system of intercommunicating voids so producing a solid, shape-retaining porous structure. Such a porous structure which may be of thermoplastics material or a thermosetting polymer made by any suitable method may be employed in the air freshener unit of this invention.

The preferred porous synthetic polymeric materials for use as support component of the unit of this invention are those made by bonding together solid particles of synthetic polymer. The bonding may be effected, for instance, by casting in a mould; moulding under atmospheric or elevated pressure; sintering under the application of heat with optional application of elevated or reduced pressure; or by casting or by moulding solid polymer particles in the presence of a bonding agent such as a drying oil of vegetable origin or a polymer solution.

The preferred process of producing porous, synthetic polymer supports for use in the units of this invention is the said sintering technique, or the moulding method or a combination of these techniques using, as starting material, a synthetic thermoplastic polymer in particulate form. The chemical composition of the synthetic polymer can vary widely. Thus, suitable polymers include polyamides, polyesters, polystyrene, acrylonitrile-butadiene-styrene (ABS) terpolymers, addition polymers of vinyl-substituted monomers, e.g. polyvinyl chloride and polyvinyl acetate and, especially, polyolefins; always provided that the polymer is readily bondable into a porous structure which is chemically resistant to the fragrance to be applied to it.

The particularly preferred porous synthetic polymer supports are those produced by sintering or moulding polyolefin particles, into sheet, rod or tube form, especially into a cylindrical shape having domed ends.

One convenient starting material is particulate high density polyethylene in which at least 80% by weight of the particles are sized in the range of from 1 to 500 micron and usually at least 90% by weight of the particles have particle size within the range of from 50 to 350 micron. These particles are themselves agglomerates of smaller particles.

The shape of the preferred porous polyolefin support for the unit of the present invention is determined by the shape of a multi-part mould which may be made, e.g. of glass or metal. To produce porous polyolefin supports, an appropriate weight of polyolefin particles is fed into a mould which may then be heated, e.g. to a temperature within the range of from 150° to 250° C. over a period within the range of, for instance, 5 second to 15 minute.

For convenience of manufacture, and ease of transport and handling in use, the weight of the unit of the invention is desirably as low as possible.

The moulded and sintered porous synthetic polymeric supports for use in the unit of this invention suitably weigh from 0.5 to 7.0 gram (before application of fragrance), more preferably from 1.5 to 4.0 gram and especially from 2.0 to 3.0 gram. The supports may contain, in their interior, a quantity of unbonded particles. The voild volume of the supports may be between 25% to 70%, more usually between 30% and 55%. The average pore size of the supports is usually between 10 and 100 micron.

Depending on the type of porous synthetic polymer used as the support for the unit of the invention, the fragrance absorption capacity of the support can vary within wide limits e.g. from 20% to 180% weight/weight, more preferably from 30% to 75% weight/weight. The fragrance absorption capacity is preferably relatively high.

The unit of the present invention may be formed in any convenient shape, so as to furnish adequate available surface area, e.g. in cylindrical-, spherical-, tubular-, disc- or strip form. In practice, however, we prefer to use a cylindrical form having domed ends.

Any conventional air-freshening fragrance may be used to impregnate the support. The fragrances used consist of naturally occurring essential oils and/or synthetically produced odoriferous substances, and usually contain one or more fixatives. Typically suitable fragrances are Floral, Citrus, Cologne, Fruity, Herbal, Evergreen, Balsamic or any combination of these.

Some basic formulations of conventional fragrances in percentages by weight are:

Floral Rose

Geraniol 40, Oil of Palma Rose 20, Phenyl ethyl alcohol 15, Ionone 5, Linalol 5, Oil of Germanium 5, Geranyl acetate 5, Hydroxy citronellal 2, Phenyl ethyl acetate 2, Musk ketone 1.

Floral Lavender

Oil of Lavandin 45, Linalyl acetate 15, Geraniol 6, Linalol 18, Oil of Geranium 2, Musk ketone 2, Coumarin 5, Bay Oil 2, Terpineol 2, Terpinyl acetate 2, Ethyl Vanillin 1.

Floral Honeysuckle

Hydroxy citronellal 20, Terpineol 20, Amyl cinammic aldehyde 15, Geraniol 10, Linalol 10, Phenyl ethyl alcohol 10, Ionone 5, Benzyl acetate 5, Methyl anthranilate 3, Vanillin 1, Musk ketone 1.

Cologne

Bergamot Oil 22, Linalyl acetate 18, Oil of Petitgrain 13, Orange Oil 12, Linalol 7, Oil of Lavender 5, Neroli 5, Citral 5, Lemongrass Oil 5, Oil of Lime 2, Oil of Clary sage 2, Oil of Lemon 2, Geraniol 2.

Evergreen

Isobornyl acetate 40, Pine Oil 20, Cedarwood Oil 10, Terpineol 10, Cedar Leaf Oil 5, Oil of Juniper Berry 5, Eucalyptus Oil 5, Oil of Rosemary 1, Oil of Camphor 1, Oil of Lemon 1, Orange Oil 1, Ionone 1.

Citrus

Lemon terpenes 20, Citronellal 15, Bergamot Oil 15, Lemongrass Oil 15, D-Limonene 10, Citral 10, Orange Oil 10, Litsea Cubeba Oil 5.

In the preferred use embodiment of the present invention, the unit is removed from any packaging and is inserted into the dust collection chamber or dust bag of a vacuum cleaner. Each time the vacuum cleaner is subsequently switched on, fragrance is released into the air which is drawn through the dust collection chamber, or dust bag, and re-released into the atmosphere of the room being cleaned. In this way, fragrance is distributed around the cleaned room to provide a rapid air-freshening effect. Due to the high fragrance-loading capacity of the porous synthetic polymer support and adequate exposed surface area, sufficient fragrance absorbed on the support allows a protracted release of fragrance at an adequately constant rate of release of fragrance, until the dust collection chamber or dust bag is full. When the dust or dustbag is discarded the air-freshener unit is also discarded.

The following Examples further illustrate the present invention.

EXAMPLES 1 TO 5

The following units according to the invention were prepared by drip-impregnation with a fragrance.

Example 1: 2.0 g porous sintered polyethylene + 1.35 g Lavender (International Flavors & Fragrances IFF (Nederland) B.V. Lavender HS298)

Example 2: 1.9 g porous sintered polyethylene + 1.46 g Floral (Naarden Florissimo 505542/A445211)

Example 3: 1.9 g porous sintered polyethylene + 1.54 g Rose (Firmenish Rose 64-370)

Example 4: 1.9 g porous sintered polyethylene + 1.53 g Honeysuckle (Bush, Boake Allen Honeysuckle 8462)

Example 5: 1.9 g porous sintered polyethylene + 1.55 g Floral (Naarden Florissimo 505542/A445211)

Each of these impregnated units having cylindrical, domed end shape was placed, separately, into the dust bag of a standard domestic vacuum cleaner where it was suspended. The weight of fragrance released, in mg per cycle (each cycle of 20 minutes duration), was determined. Twenty cycles were performed and the weight of fragrance released on average over each consecutive set of four cycles was determined.

For the purpose of comparison, parallel trials were also conducted using, as air-freshener units, commercially-available paper supports which were drip-impregnated with a Lavender fragrance (International Flavors & Fragrances IFF (Nederland) B.V. Lavender HS298). The results are set out in the following Table 1.

TABLE 1

| Example | 1 | 2 | 3 | 4 | 5 | Paper 15 mm dia × 20 mm | Paper 12 mm dia × 33.3 mm | Paper 10 mm dia × 50 mm | Paper 6 mm dia × 100 mm |
|---|---|---|---|---|---|---|---|---|---|
| Surface area ($cm^2$) | 21.65 | 21.65 | 21.65 | 21.65 | 21.65 | 12.96 | 14.83 | 17.28 | 19.41 |
| Weight fragrance (g) | 1.35 | 1.46 | 1.54 | 1.53 | 1.55 | 2.25 | 2.59 | 2.57 | 2.73 |
| Fragrance mg/$cm^2$ | 62 | 67 | 71 | 71 | 72 | 173 | 175 | 142 | 117 |
| Release of fragrance Average over 4 cycles (mg per cycle) | | | | | | | | | |
| Cycles 1–4 | 33 | 14 | 9 | 11 | 16 | 86.5 | 122 | 113 | 96 |
| Cycles 5–8 | 25 | 12 | 9 | 10 | 14 | 58 | 86 | 68 | 56 |
| Cycles 9–12 | 19 | 11 | 8 | 11 | 12 | 33 | 51 | 31 | 45 |
| Cycles 13–16 | 17 | 10 | 8 | 10 | 12 | — | — | — | — |
| Cycles 17–20 | 15 | 8 | 8 | 10 | 11 | — | — | — | — |

These results clearly show that units according to the invention provide a more consistent release rate of fragrance than units having a paper support which tend to release excessive, over-powering amounts of fragrance in the first few cycles. By contrast, the units of the invention provide an initial, acceptable level of fragrance which level is maintained throughout the life of the product until it is discarded.

EXAMPLES 6 TO 9

The following porous polymer units, produced by coagulation, were drip-impregnated with a Floral fragrance (Naarden Florissimo 505542/A445211):

Example 6: 2.2 g of porous polyurethane strip of thickness 1.2 mm was impregnated with 1.5 g Floral fragrance;

Example 7: 2.3 g of porous polyurethane strip of thickness 1.1 mm was impregnated with 1.5 g Floral fragrance;

Example 8: 2.0 g of porous polyurethane strip of thickness 0.9 mm (both surfaces sanded) was impregnated with 1.5 g Floral fragrance;

Example 9: 2.5 g of porous polyurethane strip produced by coagulaton and of thickness 2.0 mm was impregnated with 1.5 g Floral fragrance.

Each of these impregnated strips was evaluated in the vacuum cleaner test described in Examples 1 to 5. The results are set out in the following Table 2.

TABLE 2

| Example | 6 | 7 | 8 | 9 |
|---|---|---|---|---|
| Surface Area (cm$^2$) | 92 | 71.5 | 108 | 66 |
| Weight Fragrance (g) | 1.52 | 1.52 | 1.54 | 1.53 |
| Weight Support (g) | 2.22 | 2.32 | 2.04 | 2.45 |
| Fragrance (mg/cm$^2$) | 16.5 | 21.3 | 14.3 | 23.2 |
| Release of fragrance Average over 4 cycles (mg/cycle) | | | | |
| Cycles 1-4 | 55 | 59 | 48 | 41 |
| Cycles 5-8 | 42 | 61 | 52 | 42 |
| Cycles 9-12 | 45 | 38 | 45 | 34 |
| Cycles 13-16 | 35 | 36 | 36 | 31 |
| Cycles 17-20 | 26 | 24 | 34 | 27 |

Again these units of the invention provide an initial acceptable level of fragrance and this level is maintained for a considerable period of time.

EXAMPLE 10

A unit according to the invention was prepared by soaking with a fragrance (International Flavors & Fragrances IFF (Nederland) B.V. IFF-J3): 2.86 g porous sintered polyethylene having domed ends cylindrical shape and measuring in length, 4.85 cm overall and diameter 1.2 cm, was impregnated by soaking with 2.23 g of a fragrance, i.e. until no more fragrance was absorbed and the surface of the support was not dripping liquid fragrance.

The impregnated unit was simply put into the dust bag of a standard domestic vacuum cleaner. The weight of fragrance released in mg per cycle (each of 15 minute duration), was determined. Seven cycles were performed and the weight of fragrance released from three parallel experiments was measured and the average determined for each cycle.

For the purpose of comparison, parallel trials were conducted using, as air-freshener units, commercially available sheaves of cellulose fibres parallel-laid in an open-ended imperforate, cylindrical plastics sleeve; 0.99 g of such support with length 4.0 cm and diameter 1.0 cm was impregnated with 2.17 g of the same fragrance as above using the same soaking technique.

The mean results are set out in Table 3 below.

TABLE 3

| | Example 10 | Comparison |
|---|---|---|
| Exposed surface area (cm$^2$) | 18.28 | 1.57 |
| Weight fragrance (g) | 2.23 | 2.17 |
| Fragrance (mg/cm$^2$) | 122 | 1380 |
| Weight of Support | 2.86 | 0.99 |
| Release of fragrance Mean of 3 experiments (mg/cycle) | | |
| Cycle 1 (15 min) | 116 | 14 |
| Cycle 2 (30 min) | 73 | 13 |
| Cycle 3 (45 min) | 54 | 80 |
| Cycle 4 (60 min) | 46 | 148 |
| Cycle 5 (75 min) | 49 | 163 |
| Cycle 6 (90 min) | 45 | 75 |
| Cycle 7 (105 min) | 45 | 62 |

In this practical in-use test the units of the invention show a relatively constant release of perfume rapidly settling down after the initial two cycles during which the emanation was high but not insufferable to a typically constant value. By contrast the comparison unit scarcely emanates initially then increases emanation to unbearable levels of fragrance and does not settle down at all to anything like a constant level.

The particular combinations of fragrance and support in the airfreshener unit the subject of the present invention, are generally observed to possess remarkable and surprisingly constant release of fragrance by comparison with prior Art combinations. This is believed to be due at least in part to the high fragrance loading capacity of the support component of the unit and the availability of a relatively large superficial area on the support units. It has been observed that the effective life of the unit of the present invention is no less than any known device sold on the open market for the same purpose.

The porous sintered polyethylene used in examples 1-5 was obtained from Porvair Limited of King's Lynn in the United Kingdom and is sold under the trademark VYON. The porous polymer units used in examples 6 to 9 were obtained from Porvair Limited of King's Lynn in the United Kingdom and are sold under the trademark PERMAIR F, and the sintered polyethylene support soaked in example 10 was also obtained from Porvair Limited of King's Lynn in the United Kingdom and sold under the trademark VYON.

We claim:

1. A vacuum cleaner having a dust bag, said dust bag having inserted therein a dynamic air freshener unit comprising a shaped porous synthetic polymer support impregnated with a fragrance, wherein the synthetic polymer support is produced by bonding together small particles of solid polymer or coagulating a polymer solution in a non-solvent for the polymer, such that said unit will release fragrance by the passage of air over it caused by the application of differential air pressure by said vacuum cleaner.

2. A method of imparting a fragrance to a room comprising inserting within a dust bag of a vacuum cleaner a dynamic air freshener unit comprising a shaped porous synthetic polymer support impregnated with a fragrance, wherein the synthetic polymer support is produced by bonding together small particles of solid polymer or coagulating a polymer solution in a non-solvent for the polymer, and vacuuming said room with the vacuum cleaner, such that said unit will release fragrance to said room by the passage of air over it caused by the application of differential air pressure by said vacuum cleaner.

* * * * *